United States Patent
Hubert et al.

(10) Patent No.: US 8,494,818 B2
(45) Date of Patent: Jul. 23, 2013

(54) ANALYZING SPECTRAL DATA FOR THE SELECTION OF A CALIBRATION MODEL

(75) Inventors: Philippe Hubert, Esneux (BE); Eric Ziemons, Fouron-le-Comte (BE); François Moonen, Sprimont (BE)

(73) Assignees: Université de Liège, Angleur (BE); Arlenda s.a., Liège (BE)

( * ) Notice: Subject to any disclaimer, the term of this patent is extended or adjusted under 35 U.S.C. 154(b) by 114 days.

(21) Appl. No.: 12/736,929

(22) PCT Filed: May 6, 2009

(86) PCT No.: PCT/EP2009/055504
§ 371 (c)(1),
(2), (4) Date: Nov. 23, 2010

(87) PCT Pub. No.: WO2009/144124
PCT Pub. Date: Dec. 3, 2009

(65) Prior Publication Data
US 2011/0071807 A1    Mar. 24, 2011

(30) Foreign Application Priority Data
May 28, 2008    (EP) .................................... 08157099

(51) Int. Cl.
*G06F 17/10* (2006.01)
(52) U.S. Cl.
USPC .......................................................... 703/2
(58) Field of Classification Search
USPC .......................................................... 703/2
See application file for complete search history.

(56) References Cited

FOREIGN PATENT DOCUMENTS
WO    01/16579    3/2001

OTHER PUBLICATIONS

Bodson et al. (including inventor): Comparison of FT-NIR transmission and UV—vis spectrophotometry to follow the mixing kinetics and to assay low-dose tablets containing riboflavin; Journal of Pharmaceutical and Biomedical Analysis 41 (2006) 783-790.*
Dewe et al. Using total error as decision criterion in analytical method transfer; Chemometrics and Intelligent Laboratory Systems 85 (2007) 262-268.*
M. Feinberg et al., "New advances in method validation and measurement uncertainty aimed at improving the quality of chemical data," Analytic and Bioanalytic Chemistry, 2004, vol. 380, pp. 502-514.

(Continued)

*Primary Examiner* — Hugh Jones
(74) *Attorney, Agent, or Firm* — Jacobson Holman PLLC

(57) ABSTRACT

The invention relates to a method of analyzing spectral data for the selection of a calibration model, relating spectra of a substance to a physical or chemical parameter of the substance, over a predetermined range of the physical or chemical parameter, comprising the steps: a) capturing spectral data of the substance with respective values of the physical or chemical parameter over the predetermined range, b) creating a plurality of calibration models using the captured spectral data in dependence upon the values of the physical or chemical parameter based on the calibration data using statistical resampling methods, c) calculating tolerance intervals of the results at each reference level for each calibration model, and d) displaying the tolerance intervals at each reference level over the predetermined range for each calibration model. In this way, a possibility for analyzing spectra data is provided which is useful in spectroscopic applications for automated calibration model selection and makes analytical interpretation and evaluation easier and more accurate.

10 Claims, 2 Drawing Sheets

OTHER PUBLICATIONS

E. Rozet et al., "Improvement of decision efficiency of the accuracy profile by means of a desirability function for analytical methods validation," Analytica Chimica Acta, Apr. 7, 2007, vol. 591, No. 2, pp. 239-247.

E. Rozet et al., "Using tolerance intervals in pre-study validation of analytical methods to predict in-study results," Journal of Chromatography A, Mar. 30, 2007, vol. 1158, No. 1-2, pp. 126-137.

C. Bodson et al., "Validation of manufacturing process of Diltiazem HCl tablets by NIR spectrophotometry (NIRS)," Journal of Pharmaceutical and Biomedical Analysis, May 21, 2007, vol. 45, No. 2, pp. 356-361.

P. Hubert et al., "Harmonization of strategies for the validation of quantitative analytical procedures: A SFSTP proposal—Part I," Journal of Pharmaceutical and Biomedical Analysis, 2004, vol. 36, pp. 579-586.

P. Hubert et al., "Harmonization of strategies for the validation of quantitative analytical procedures: A SFSTP proposal—Part II," Journal of Pharmaceutical and Biomedical Analysis, 2007, vol. 45, pp. 70-81, Jun. 2007.

P. Hubert et al., "Harmonization of strategies for the validation of quantitative analytical procedures: A SFSTP proposal—Part III," Journal of Pharmaceutical and Biomedical Analysis, 2007, vol. 45, pp. 82-96.

J. Guttmann, "Tolerance Regions, Statistical," *Encyclopedia of Statistical Sciences*, Ed. 1988, vol. 9, pp. 272-287.

R. Mee, "$\beta$-Expectation and $\beta$-Content Tolerance Limits for Balanced One-Way ANOVA Random Model," Technometrics, Aug. 1984, vol. 26, No. 3, pp. 251-254.

D.A. Burns et al., "Handbook of Near-Infrared Analysis," Practical Spectroscopy Series vol. 27, Marcel Dekker: New York, 2001, pp. 135-150, 215-229, 297-306, 499-501, 523-527, 533-535, 588-594, 647-655, 189-205, 135-150, 189-205, 521-523, 533-535, 594-596, as presented. Not all pages are present and others are duplicates. Nevertheless, the submitted pages were considered.

* cited by examiner

ANALYZING SPECTRAL DATA FOR THE SELECTION OF A CALIBRATION MODEL

This is a national stage of PCT/EP09/055,504 filed May 6, 2009 and published in English, which has a priority of European no. 08157099.6 filed May 28, 2008, hereby incorporated by reference.

FIELD OF THE INVENTION

The present invention relates to the field of analyzing spectral data for the selection of a calibration model, relating spectra of a substance to a physical or chemical parameter of the substance over a predetermined range of the physical or chemical parameter. In particular, the present invention relates to apparatus, methods and software for analyzing spectral data for the selection of a calibration model, and/or relating spectra of a substance to a physical or chemical parameter of the substance over a predetermined range of the physical or chemical parameter.

BACKGROUND OF THE INVENTION

It is generally known that one type of spectroscopy can be defined as a study of electromagnetic wave interactions with material. When electromagnetic radiation such as light reaches the material, energetic transitions occur, transitions which are different according to the type of light. The near infrared (NIR) region (780-2500 nm) is situated between the red band of visible light and the mid infrared region. Molecular vibrations of hydrogen bonds, such as C—H, N—H, O—H and S—H, give birth to the NIR spectrum.

NIR spectroscopy offers many advantages such as no sample preparation, no sample destruction, fast data acquisition, and the use of optical fibers allows "online" analysis. Moreover, NIR spectra contain both physical and chemical information. Physical information can be granulometry, particles shape, polymorphism etc., and, on the other hand, chemical information can be the active pharmaceutical ingredient, moisture etc. However, each technique has its drawbacks:

In general, it is a problem that the NIR system must be calibrated. Optimisation and calibration are time-consuming tasks because the development of the predictive model has to take into account the use of a suitable reference method (e.g. chromatography, titration) to assign quantitative values of the chemical or physical parameter of interest for the spectral data. Moreover, due to the great quantity of physical and chemical information included in the NIR spectra, a visual interpretation is difficult. Basically, only a small piece of information is relevant for the objective investigated. For this purpose chemometric tools (e.g. MLR, PLS, PCR, ANN) are used to extract the significant information arising from the physical and chemical data using multivariate approaches. Chemometrics is the use of mathematical and statistical methodologies applied in general to chemical data. These tools include methods adapted for cleaning, classifying, interpreting and extracting information from data or signals. Two widely used chemometric tools for spectral analyses are mathematical pretreatment and regression methods. The first one consists in suppressing the biggest part of the information that is not directly linked to the chemical nature of the sample. Examples of mathematical pretreatments or data pretreatments include Savitzky-Golay smoothing filter, standard normal variate (SNV) and multiplicative scatter correction (MSC). The second one, i.e. the regression methods or data regression models, links a spectrum to a concentration of interest determined by the reference method, allowing the creation of a mathematical model that is useful for calibration purposes. Examples for regression methods include multiple linear regression (MLR), partial least squares (PLS) regression and artificial neuronal network (ANN), as described in D. A. Burns, E. W. Ciurczak, "Handbook of Near-Infrared Analysis", Practical Spectroscopy Series Vol. 27, Marcel Dekker: New York, 2001.

In the pharmaceutical field, conformity analyses realized between batch production and batch release can be time consuming if all of them are performed after the manufacturing process. Thus, the concept of process analytical technology (PAT) is born, as described in American Food and Drug Administration (FDA), Guidance for Industry PAT-A Framework for Innovative Pharmaceutical Manufacturing and Quality Assurance, FDA, 2004. The aim of PAT is to enable monitoring each critical step of the fabrication in real time and, thus, reducing the batch release time. PAT gives also the opportunity to tune manufacturing parameters, and thus PAT allows avoiding the loss of batches. Regarding its non-invasive, non-destructive and fast data acquisition character, NIR spectroscopy is more and more associated with the concept of PAT.

Near infrared spectroscopy can be used to realize assays in the pharmaceutical field. The development of NIR system is generally split into 2 parts: calibration and validation of the predictive model. It is based on calibration data used to build calibration models regarding the chosen chemometric tools. After, an independent validation set of data is used for the validation of the selected model, respectively.

Original concepts of tolerance intervals based on the total error approach and the graph of the accuracy profile have been introduced to help the validation process, as described in the three Hubert Ph. et al. articles: Harmonization of strategies for the validation of quantitative analytical procedures—A SFSTP proposal—parts I-III, Journal of Pharmaceutical and Biomedical Analysis, 2004-2007. This approach can be applied on any type of analytical technique and is independent with regard to the matrix in which the analyte or substance of interest is analysed, such as in pharmaceutical formulations, biological fluids etc.

An accuracy index can be computed for each accuracy profile in order to resume all the information included in the accuracy profile in one "desirability" value. The accuracy index is therefore a basis to select the best calibration model only based on the calibration data.

SUMMARY OF THE INVENTION

It is an object of the present invention to provide apparatus, methods and software for analyzing spectral data for the selection of a calibration model, and/or relating spectra of a substance to a physical or chemical parameter of the substance over a predetermined range of the physical or chemical parameter.

It is an advantage of the present invention that it provides a convenient and easy to use possibility for selecting a calibration model from a plurality of possible calibration models. The present invention provides apparatus and methods for selecting a calibration model only based on calibration data using statistical resampling methods (e.g. cross-validation, bootstrapping).

Each calibration model correlates confirmed measured values of a physical or chemical parameter, such as granulometry, polymorphism, moisture content, ingredient content with observed spectra, such as infrared (IR), near infrared (NIR), Raman spectra, obtained during calibration experiments. Data pretreatment and regression methods provide the calibration model that will be used in future routine use with any new spectrum corresponding to an unknown amount of physical or chemical parameter to determine. In this context, the invention will provide a method to analyze spectral data and to select the best calibration model from a plurality of given calibration models.

To fulfill this objective, resampling methods such as cross-validation or bootstrapping can be used. The first method (cross-validation) involves a partition of the calibration data, with or without pretreatment(s), into complementary subsets. Regression is made on one subset (calibration set) while the results are tested on the other subset (monitor set or test set). Iteratively, different partitions can be used to globally assess the predictive quality of the regression models as long with the data pretreatments. The second method (bootstrapping), involving resampling with replacement of calibration data, with or without pretreatment, can be used as well to assess the quality of the models for prediction along with data pretreatment.

This object is solved by the subject matter of independent claim 1. Preferred embodiments are defined in the sub claims.

This object is achieved by a method of analyzing spectral data for the selection of a calibration model, relating spectra of a substance to a physical or chemical parameter of the substance, over a predetermined range of the physical or chemical parameter, preferably the predetermined range of the physical or chemical parameter comprises at least three levels, comprising the steps:
  a) capturing spectral data of the substance with respective values of the physical or chemical parameter over the predetermined range,
  b) creating a plurality of calibration models using the captured spectral data in dependence upon the values of the physical or chemical parameter based on the calibration data using statistical resampling methods,
  c) calculating tolerance intervals of the results at each reference level for each calibration model, and
  d) displaying the tolerance intervals at each reference level over the predetermined range for each calibration model.

It is noted that the term "reference level", preferably used in connection with a chemical and/or physical parameter, is defined as the concentration or amount of the chemical or physical parameter determined by the reference analytical method. Each reference concentration or amount level is computed using the relevant reference analytical method by applying its analytical procedure. For instance, this is an HPLC analytical procedure for the quantitation of a defined chemical substance. This reference level, determined in this way is assumed as the true concentration or amount of the chemical or physical parameter present in the sample under investigation.

Further, it is noted that the term "tolerance interval" is defined as a statistical interval covering at least a specified proportion of a population, either on average or else with a stated level of confidence. It thus comprises beta-expectation tolerance interval and beta-gamma content tolerance intervals. For a full statistical definition of a tolerance interval the reader shall refer to Guttman I., Tolerance Regions, Statistical, Encyclopedia of statistical sciences, 1988, eds. S. Kotz, N. L. Johnson and C. B. Read, John Wiley & Sons, volume 9, pages 272-287.

It is an important idea of the invention to provide a method which uses a mathematical model to compute accuracy profiles on which the spectral data measured can be analyzed using resampling methods using only the calibration data, also referred to as calibration data set or calibration set in the following, with or without spectral data pretreatment. Then a user can apply the total error concept, as described in Hubert Ph. et al., Journal of Pharmaceutical and Biomedical Analysis 36 (2004) 579; Hubert Ph. et al., Journal of Pharmaceutical and Biomedical Analysis 45 (2007) 70, to the observed calibration results using each one of the bunch of known data pretreatment and data regression models with various input procedures. Applying the total error concept results in plots of the tolerance intervals which are described in more detail further below. Hence, any tolerance interval, such as for example beta expectation tolerance limits can be calculated and plotted in a graph.

According to a preferred embodiment of the invention, after computing the tolerance intervals at each reference level, the lowest value of the relative total error or the highest value of the Fitting Model Index, FMI for short, is regarded. The FMI, also called desirability index, corresponds to the geometric mean of the dosing range, precision and trueness indexes and its value range from 0 to 1 depends on the fit quality. This dimensionless number is alternatively used for comparing different models. It is noted that the calibration model is better the closer the FMI is to 1. The FMI is built according to Rozet E. et al., Analytica Chimica Acta 591 (2007), 239.

Then the model which shows the smallest relative total error or the Fitting Model Index, FMI closest to 1, respectively, is selected. This can be done manually by a user or also automatically by means of a computing unit. Therefore, the best calibration model comprising either none or any spectral data pretreatment together with a subsequent data regression model is selected. In other words, a method for developing quantitative models is proposed. An approach based on the accuracy profile concept is used in order to select the best data regression model and the best data pretreatment to build the best calibration model. It is also possible that, based on the application and/or requirements, no spectral data pretreatment is required.

In one preferred embodiment of the invention the spectral data comprises near infrared (NIR) spectra data. It goes without saying that, in general, the method can be applied on any desired wavelength range.

The calibration model preferably comprises at least one of a data regression model and a data pretreatment. According to other preferred embodiments of the invention, no spectral data pretreatment is necessary. The calibration model can comprise a data regression model. The data regression model preferably comprises either none or any spectral data pretreatment followed by at least one of a multiple linear regression (MLR) model, a partial least squares (PLS) model, a principal component regression (PCR) model and an artificial neuronal network (ANN) model. The data pretreatment preferably comprises none or any one of a standard normal variate (SNV) treatment, a Savitzky-Golay (SG) smoothing filter with no derivative (SG0) and/or a first derivative (SG1) and/or a second derivative (SG2) operation, a multiplicative scatter correction (MSC), an orthogonal signal correction (OSC) or raw data. The term "raw data" means that the spectral data is left without performing any mathematical pretreatment.

In yet another preferred embodiment of the invention, the tolerance interval corresponds to a beta expectation tolerance interval or a beta-gamma content tolerance interval. However, any other tolerance interval can be used as well.

According to yet another preferred embodiment of the invention, the step of displaying the tolerance intervals at each reference level over the predetermined range of the physical or chemical parameter, that is characterizing the substance, for each calibration model comprises at least one of printing on a printer, plotting on a plotter, displaying on a video display unit and projecting onto a screen. The method preferably further comprises the selection of the calibration model upon a predefined criterion. The predefined criterion preferably comprises at least one of a beta tolerance interval corresponding to a small relative error of the calibration model, an acceptance limit of the physical parameter corresponding to a small relative total error of the calibration model and a Fitting Model Index of the calibration model that is close to 1. This serves for optimizing the model in order to find the best combination of data pretreatment and data regression with the optimum amount of data or data sets and the optimum number of factors needed for the different models. The selection of the best calibration model can be done manually by a user and/or automatically.

According to yet another preferred embodiment of the invention, the methodology to compute the Fitting Model Index (FMI), preferably also called desirability index, corresponds to the geometric mean of the dosing range, precision and trueness indexes and its value range from 0 to 1 depending on the fit quality. This dimensionless number is alternatively used for comparing different models. It is noted that the calibration model is better the closer the FMI is to 1. The FMI is built according to Rozet E. et al. Analytica Chimica Acta, 591 (2007), 239-247.

According to yet another preferred embodiment of the invention, the methodology to compute a tolerance interval is frequentist or Bayesian. Preferably, the reference level is the concentration or amount of the physical or chemical parameter determined by the reference analytical method. Each reference concentration or amount level is computed using the relevant reference analytical method by applying its analytical procedure. For instance, this is a High-performance liquid chromatography, HPLC for short, analytical procedure for the quantitation of a defined chemical substance. This reference level, determined in this way, is preferably assumed as the true concentration or amount of the physical or chemical parameter present in the samples under investigation.

The present invention also provides a computer program product comprising code segments that when implemented on a computing system implement any of the methods of the present invention. The present invention also includes the computer program product stored on machine readable signal storage means.

The present invention provides a computer based system for analyzing spectral data for the selection of a calibration model, relating spectra of a substance to a physical or a chemical parameter of the substance, over a predetermined range of the physical or chemical parameter, comprising:
a) means for capturing spectral data of the substance with respective values of the physical or chemical parameter over the predetermined range,
b) means for creating a plurality of calibration models using the captured spectral data in dependence upon the values of the physical or chemical parameter based on the calibration data using statistical resampling methods,
c) means for calculating tolerance intervals of the results at each reference level for each calibration model, and
d) means for displaying the tolerance intervals at each reference level over the predetermined range for each calibration model.

It is an important idea of the invention to provide a possibility for analyzing spectral data that is useful in spectroscopic applications and makes analytical interpretation and evaluation easier, more accurate and reliable.

According to a preferred embodiment of the invention near infrared (NIR) spectroscopy in one or more of the following applications is proposed: pharmaceutical industry, especially for determining concentration levels and/or moisture levels of at least one ingredient in a formulation; biological industry, especially for analyzing fluids; food industry; and fuel industry.

Finally, it is worth noting that the method provides highly accurate and reliable results and, thus, makes its application in spectroscopic investigations important and useful.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Embodiments of the present invention will be described in detail with respect to certain drawings but the invention is not limited thereto. For illustrative purposes, most of the drawings are schematic, therefore, the size of the elements are not drawn to scale. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

The term "comprising", used in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Figure 1:
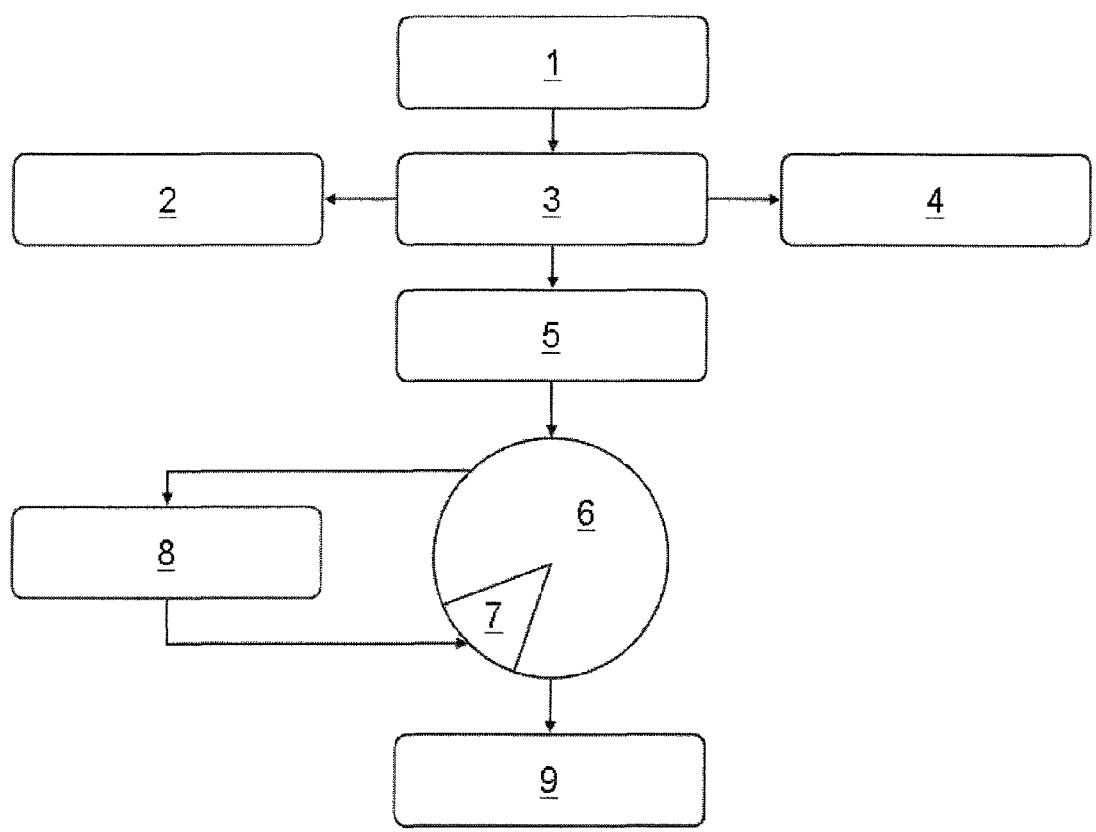
FIG. 1 depicts the major steps of a NIR calibration procedure according to an embodiment of the invention.

FIG. 1 summarizes the major steps of a NIR calibration procedure in an embodiment of the invention. First, a purpose definition 1 is made: a balanced design of p×n (number of series x number of replicates per series) independent experiments are set up and NIR spectra 2 are recorded for each reference level $j=1, \ldots, n_{cl}$ of one or more analyte(s) in a pharmaceutical formulation of interest. Further, a sample analysis 3 is performed for the series. The series can represent different independent laboratories or different days, operators etc. There are then $N=p \times n \times n_{cl}$ experiments to be realised. Further, a reference method 4 is applied for the sample analysis 3.

Each experiment results in a spectrum $x_i$ (i=1, ..., N) of size q, which is the intensity of the signal across each wavelength recorded by the photo-sensitive detector of the spectrometer. The recorded signal is then the original NIR signal, which has been absorbed and reflected, or transmitted, when projected on or through the sample, respectively.

The matrix X (N×q) can be defined as the set of spectra, disposed as the rows of X. Then, for each spectrum corresponding to one concentration level of the introduced analyte, the true concentration of the analyte is determined with the reference method 4. Informative spectral regions can also be selected in the complete set 5 of recorded spectra in order to simplify the data pretreatment and the data regression process. Using cross-validation the model is selected 9 upon a predetermined range of the physical parameter that is characteristic for the substance under test. In this embodiment the physical or chemical parameter is the moisture content of the analyte, i.e. the substance under test, in a pharmaceutical formulation. Thus, the model is built and optimized 8 with the calibration set 6 and monitor set 7 (or test set). Finally, the best calibration model is selected 9. Alternatively, some pretreatments or treatments can be realized on the data to remove the noise information or noise content, respectively. This serves for increasing the signal quality and/or for reducing the amount of data which makes the signal processing easier to handle.

In this embodiment the following well-known data pretreatments are used:

The standard normal variate (SNV) transformation is applied to each spectrum.

Alternatively, the Savitzky-Golay filter is a parametric function which performs local polynomial regressions to smooth the signal. Moreover, it is also able to estimate its derivatives, such as the first and second derivatives, after smoothing.

Other signal processing methods for data pretreatment are also available and can be used, such as multiplicative scattering correction (MSC) or orthogonal signal correction (OSC). In the following, it will be shown how the accuracy profile concept helps to select a calibration model comprising a data pretreatment model.

As NIR spectroscopy only gives spectral results, the NIR system must be calibrated. Hence, a reference method is needed that links results of interest with the spectral data. As it is desirable that the calibration is not repeated every day, it has to use conditions and samples representative of the ones found in routine, otherwise future results would be considered as wrong and/or as outliers. As already mentioned, NIR spectra contain a great quantity of information needing the use of chemometric tools in order to adequately link the spectra to the relevant information. The set of spectra that has been pretreated or not is split in a calibration set 6 and a monitor set 7 as shown in FIG. 1. In this embodiment PLS regression on the calibration set 6 to fit a model f is performed. Thus, the physical or chemical parameter is regarded as a function of the model f with a matrix X as parameter: f(X). The physical or chemical parameter corresponds to a column vector that matches each spectra (lines of X). It contains observed values of the physical or chemical parameter which have been determined by a reference method, namely the reference level. Principally, PLS regression establishes a linear relation between the matrix X and the response vector of the physical or chemical parameter. It finds out from X the factors (also called scores), linear combinations of the variables of X, that best describe the response of the physical or chemical parameter and that are also uncorrelated. This gives accurate and reliable results in terms of predicting new responses.

One general task when applying e.g. conventional PLS regression methods is to know how many factors must be selected to obtain the best predictions. Classical methodologies advise to use predictive error-based criteria such as the root means square error of cross-validation (RMSECV), the predictive error sum squares (PRESS), the standard error of prediction (SEP) or other criteria such as the determination coefficient $R^2$, bias, and so on, computed on a monitor set 7. Cross-validation is also generally used. If the quality of the PLS model can be highly increased in optimizing these criteria, it does not seem clear that they are perfectly aligned with the purpose of the considered analytical method: i.e. if the model quantifies accurately.

Therefore, the concept of fit-for-purpose has been proposed to select the most relevant model(s) during the calibration process, i.e. choosing a model based only on the quality of the predicted results that this model will allow to obtain. In practice, the method uses a predefined criterion upon which the selection of the calibration model is performed, the predefined criterion comprises at least one of a tolerance interval corresponding to a small relative error of the calibration model, an acceptance limit of the physical or chemical parameter corresponding to a small relative total error of the calibration model and a Fitting Model Index of the calibration model that is close to 1. The model which gives the best future predictive results is kept for further evaluations. This ensures that this calibration model is fitted for its very purpose: providing accurate and reliable results. The Fitting Model Index, also called desirability index, corresponds to the geometric mean of the dosing range, precision and trueness indexes and its value range from 0 to 1 depending on the fit quality. This dimensionless number is alternatively used for comparing different models. It is noted that the calibration model is better the closer the Fitting Model Index is to 1. The Fitting Model Index is built according to Rozet E. et al., Analytica Chimica Acta, 591 (2007), 239-247. By selecting another criterion based on the observation of the fitting model index versus a number of factors, this will allow the determination of the optimum predetermined number of factors that is used in the selected calibration model. These factors can e.g. be the number of PLS components.

In the following the relevant terminology and definitions are described.

Figure 2:
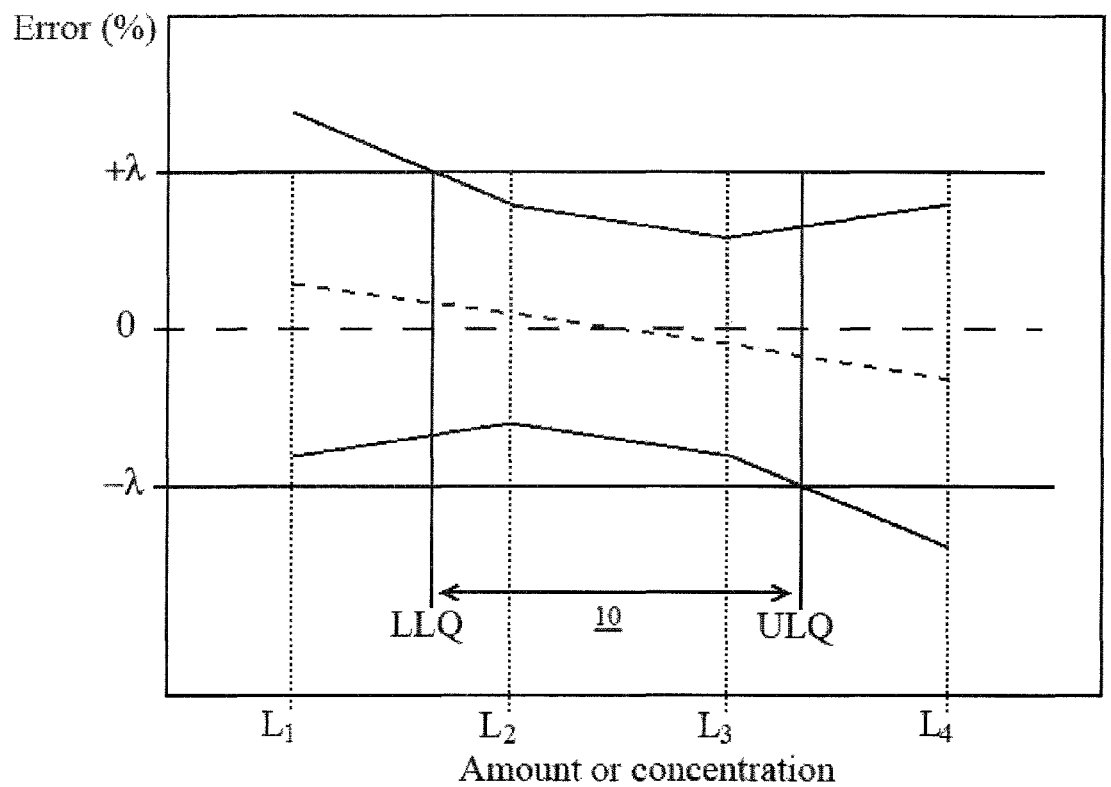
FIG. 2 illustrates the accuracy profile concept as a decision tool for selecting the best calibration model according to an embodiment of the invention.

The trueness of an analytical procedure expresses the closeness of agreement between the mean value obtained from a measurement series and the value which is accepted either as a conventional true value or an accepted reference value (international standard) or a reference value obtained by a reference method. The measure of trueness is generally expressed in terms of recovery and of absolute or relative error (systematic error), also called bias as depicted in FIG. 2.

The precision of an analytical procedure, on the other hand, expresses the closeness of agreement between a measurement series obtained from multiple samplings of the same homogeneous sample under nearly the same conditions. The closeness of agreement can be dispersion level, relative standard deviation etc. The precision gives some information on random errors and it can be evaluated at least three levels: repeatability, intermediate precision (within laboratory) and reproducibility. The precision only represents the distribution of random errors and has no relation with a true or specified value. The measure of precision is calculated from the standard deviation of the results.

Furthermore, the accuracy of an analytical procedure expresses the closeness of agreement between the value found and the value which is accepted either as a conventional true value or an accepted reference value. The closeness of agreement observed is the result of the sum of the systematic and random errors. In other words, the total error is linked to the result. Consequently, the accuracy is the expression of the sum of trueness and precision.

Moreover, the limit of quantization of an analytical procedure is the lowest amount of the targeted substance in the sample which can be quantitatively determined under almost the same experimental conditions with a well defined accuracy.

Further, the range (reference numeral 10 in FIG. 2) of an analytical procedure is the range between the lower and the upper concentration limits, including these limits, for which it has been demonstrated that the analytical procedure has a suitable level of accuracy, i.e. trueness and precision.

FIG. 2 illustrates the accuracy profile concept as a decision tool in one embodiment of the invention. LLQ represents the lower limit of quantification and ULQ the upper limit of quantification. Both are shown together with the range 10 in FIG. 2. The range 10 comprises both the LLQ and the ULQ. The resampling process is performed to choose the most accurate regression model along with signal pretreatment(s), if any, in order to define the most adequate calibration model. In this embodiment the accuracy profile concept based on the total error concept is applied. The total error of an analytical measurement (i.e. the accuracy) is defined as a sum of the systematic error (i.e. the trueness) and the random error (i.e. precision). In the preferred embodiment, it is preferably the beta-expectation tolerance intervals that have been introduced in Robert Mee, "Technometrics", 1984, vol. 26, pp. 251-254. The tolerance intervals are used to estimate the effect of the total error on future results and together with the already mentioned Hubert Ph. et al. articles they propose a way to compare it with a predefined acceptance limit X of the physical parameter in a predetermined range of a substance under test. Nonetheless any other methodology to compute beta-expectation tolerance interval or any tolerance interval is included such as and not limited to frequentist or Bayesian methodologies.

As illustrated in FIG. 2, the accuracy profile constructed from the tolerance intervals on the expected measures allows deciding the capability of an analytical procedure to give results inside acceptance limits $\lambda$. The area over the range 10 describes the range in which the procedure is able to quantify with a known accuracy and a risk fixed a priori by the analyst. If the analyst is ready to assume, for example a risk of 5%, he will be able at the end of the resampling procedure to guarantee that 95 times out of 100 the future measures given by his procedure will be included within the acceptance limits $\lambda$ fixed according to the regulatory requirements. These can e.g. be 1% or 2% on bulk, 5% on pharmaceuticals specialties, 15% in bioanalysis, environment, etc. Since the "true bias" and the "true precision" of an analytical procedure are unknown, the accuracy profile shown in FIG. 2 by reference level ($C_1$, $C_2$, . . . ) is obtained by computing the tolerance interval that allows to evaluate the proportion of expected measures inside the acceptance limits ($\pm\lambda$). This accuracy profile is constructed from the available estimates of the bias or relative error and precision of the analytical procedure at each reference level at the end of the calibration model selection phase using tolerance intervals.

In other words, the accuracy profile shown in FIG. 2 can be obtained by joining together, on one hand, the relative lower tolerance limits and, on the other hand, the relative upper tolerance limits, in a plot of the relative total error versus the predetermined range of the physical or chemical parameter, corresponding to the reference level that is the concentration level in this embodiment. The predefined acceptance limits $\lambda$ are also added to the graph. This gives a visual tool allowing the assessment of the validity of the method: it is expected on average that a proportion $\beta$ (beta) of future measurements will effectively fall in the beta-expectation tolerance intervals. If this interval is included in the $\lambda$ acceptance limits, it ensures that the conditions of a plausibly acceptable calibration model are fulfilled. However, as this visual approach can suffer from subjectivity of the user, different criteria can be defined to formally assess how desirable an accuracy profile of an analytical method could be. The size of the dosing range (range 10 from lower to upper limit of quantification, i.e. from LLQ to ULQ), the trueness (systematic error of the method) and the precision (random error) can be used as desirability functions to define a global desirability index or fitting model index for each accuracy profile created or plotted.

The accuracy profile, constructed from the tolerance intervals on the relative expected measures, allows deciding the capability of an analytical procedure to give results inside acceptance limits fixed a priori.

A potential use of the invention is in near infrared (NIR) spectroscopy in one or more of the following fields: pharmaceutical industry, especially for determining concentration levels and/or moisture levels of at least one analyte in a formulation, in biological industry, especially for analyzing fluids, in food industry and in fuel industry.

Hence, a robust model has been created because once a model is developed it must be able to accurately determine the physical or chemical parameter over the predetermined or predefined range, such as the moisture content or any other physical or chemical parameter of different samples during a long period of time. Each model has an optimum number of e.g. PLS factors. Considering the conventional criteria of the different data pretreatments with an optimum number of factors used in a model, it is not obvious to select the most appropriate model. Indeed, these criteria are too close to be able to make a differential decision. Consequently, the selection of the most accurate and reliable calibration model is carried out using the proposed inventive concept based on the accuracy profile. It is worth noting that the use of the accuracy profile confirms the optimum number of e.g. PLS factors for each calibration model and allows further interpretation of the model performance.

NIR spectroscopy can be used as a non-invasive, non-destructive method to quantify e.g. the moisture content in pharmaceutical pellets. With the inventive concept it is made easier for analytical interpretation while keeping all useful statistics. The use of the inventive concept allows selecting the most appropriate calibration model for spectroscopic investigations. Hence, a calibration model can be selected leading to a reasonable precision, trueness and accuracy of the prediction of the physical or chemical parameter.

The methods of the present invention can be implemented on a computing system which can be utilized with the methods and in a system according to the present invention including computer programs. A computer may include a video display terminal, a data input means such as a keyboard, and a graphic user interface indicating means such as a mouse. Computer may be implemented as a general purpose computer, e.g. a UNIX workstation or a personal computer.

Typically, the computer includes a Central Processing Unit ("CPU"), such as a conventional microprocessor of which a Pentium processor supplied by Intel Corp. USA is only an example, and a number of other units interconnected via bus system. The bus system may be any suitable bus system. The computer includes at least one memory. Memory may include any of a variety of data storage devices known to the skilled person such as random-access memory ("RAM"), read-only memory ("ROM"), non-volatile read/write memory such as a hard disc as known to the skilled person. For example, computer may further include random-access memory ("RAM"), read-only memory ("ROM"), as well as a display adapter for connecting system bus to a video display terminal, and an optional input/output (I/O) adapter for connecting peripheral devices (e.g., disk and tape drives) to system bus. The video display terminal can be the visual output of computer, which can be any suitable display device such as a CRT-based video display well-known in the art of computer hardware. However, with a desktop computer, a portable or a notebook-based computer, video display terminal can be replaced with a LCD-based or a gas plasma-based flat-panel display. Computer further includes user an interface adapter for connecting a keyboard, mouse, optional speaker. The relevant data required the digital model may be input directly into the computer using the keyboard or from storage devices, after which a processor carries out a method in accordance with the present invention. The relevant data may be provided on a suitable signal storage medium such as a diskette, a replaceable hard disc, an optical storage device such as a CD-ROM or DVD-ROM, a magnetic tape or similar. The results of the method may be transmitted to a further near or remote location. A communications adapter may connect the computer to a data network such as the Internet, an Intranet a Local or Wide Area network (LAN or WAN) or a CAN.

The computer also includes a graphical user interface that resides within machine-readable media to direct the operation of the computer. Any suitable machine-readable media may retain the graphical user interface, such as a random access memory (RAM), a read-only memory (ROM), a magnetic diskette, magnetic tape, or optical disk (the last three being located in disk and tape drives). Any suitable operating system and associated graphical user interface (e.g., Microsoft Windows, Linux) may direct the CPU. In addition, the computer includes a control program that resides within computer memory storage. The control program contains instructions that when executed on the CPU allow the computer to carry out the operations described with respect to any of the methods of the present invention.

The present invention also provides a computer program product for carrying out the method of the present invention and this can reside in any suitable memory. However, it is important that while the present invention has been, and will continue to be, that those skilled in the art will appreciate that the mechanisms of the present invention are capable of being distributed as a computer program product in a variety of forms, and that the present invention applies equally regardless of the particular type of signal bearing media used to actually carry out the distribution. The present invention provides a computer program product stored on machine readable signal storage means. Examples of computer readable signal bearing media include: recordable type media such as floppy disks and CD ROMs and transmission type media such as digital and analogue communication links.

Accordingly, the present invention also includes a software product which when executed on a suitable computing device carries out any of the methods of the present invention. Suitable software can be obtained by programming in a suitable high level language such as C and compiling on a suitable compiler for the target computer processor or in an interpreted language such as Java and then compiled on a suitable compiler for implementation with the Java Virtual Machine.

The present invention provides software, e.g. a computer program having code segments that provide a program that, when executed on a processing engine, provides a computer based system for analyzing spectral data for the selection of a calibration model that relates spectra of a substance to a physical or a chemical parameter of the substance, over a predetermined range of the physical or chemical parameter.

The software may include code segments that provide, when executed on the processing engine in communication with memory and a display, for the capture of spectral data of the substance with respective values of the physical or chemical parameter over the predetermined range, creation of a plurality of calibration models using the captured spectral data in dependence upon the values of the physical or chemical parameter based on the calibration data using statistical resampling methods, calculation of tolerance intervals of the results at each reference level for each calibration model, and the display of the tolerance intervals at each reference level over the predetermined range for each calibration model. The spectral data may comprise near infrared spectra data. The calibration model may comprise at least one of a data regression model and a data pretreatment. The software may include code segments that provide, when executed on the processing engine, that the data regression model may comprise either none or any spectral data pretreatment followed by at least one of a multiple linear regression model, a partial least squares model, a principal component regression model and an artificial neuronal network model. The software may include code segments that provide, when executed on the processing engine, that the data pretreatment comprises none or any one of a standard normal variate treatment, a Savitzky-Golay smoothing filter with no derivative and/or a first derivative and/or a second derivative operation, a multiplicative scatter correction, an orthogonal signal correction or raw data.

The tolerance interval may correspond to either a beta expectation tolerance interval or a beta-gamma content tolerance interval. The software may include code segments that provide, when executed on the processing engine, that the display of the tolerance intervals at each reference level over the predetermined range for each calibration model comprises at least one of printing on a printer, plotting on a plotter, displaying on a video display unit and projecting onto a screen. The software may include code segments that provide, when executed on the processing engine, the selection of the calibration model upon a predefined criterion. The predefined criterion may comprise at least one of a tolerance interval corresponding to a small relative error of the calibration model, an acceptance limit of the physical parameter corresponding to a small relative total error of the calibration model and a Fitting Model Index of the calibration model that is close to 1. The software may include code segments that provide, when executed on the processing engine, that the methodology to compute a tolerance interval is frequentist or Bayesian. The reference level can be the concentration or amount of the physical or chemical parameter determined by the reference analytical method.

The software may include code segments that provide, when executed on the processing engine, that the methodology to compute the Fitting Model Index corresponds to the geometric mean of the dosing range, precision and trueness indexes and its value range from 0 to 1 depending on the fit quality.

Accordingly the present invention provides a computer based system for analyzing spectral data for the selection of a calibration model, relating spectra of a substance to a physical or a chemical parameter of the substance, over a predetermined range of the physical or chemical parameter, comprising:

a) means for capturing spectral data of the substance with respective values of the physical or chemical parameter over the predetermined range, b) means for creating a plurality of calibration models using the captured spectral data in dependence upon the values of the physical or chemical parameter based on the calibration data using statistical resampling methods, c) means for calculating tolerance intervals of the results at each reference level for each calibration model, and d) means for displaying the tolerance intervals at each reference level over the predetermined range for each calibration model. The spectral data may comprise near infrared spectra data. The calibration model may comprise at least one of a data regression model and a data pretreatment. The system may be adapted so that the data regression model may comprise either none or any spectral data pretreatment followed by at least one of a multiple linear regression model, a partial least squares model, a principal component regression model and an artificial neuronal network model. The system may be adapted so that the data pretreatment comprises none or any one of a standard normal variate treatment, a Savitzky-Golay smoothing filter with no derivative and/or a first derivative and/or a second derivative operation, a multiplicative scatter correction, an orthogonal signal correction or raw data.

The tolerance interval may correspond to either a beta expectation tolerance interval or a beta-gamma content tolerance interval. The system may be adapted so that display of the tolerance intervals at each reference level over the predetermined range for each calibration model comprises at least one of printing on a printer, plotting on a plotter, displaying on a video display unit and projecting onto a screen. For this purpose the system may include a printer, a plotter, a video display unit, or a projection system including a projection screen. The system may be adapted so that the selection of the calibration model depends upon a predefined criterion. The predefined criterion may comprise at least one of a tolerance interval corresponding to a small relative error of the calibration model, an acceptance limit of the physical parameter corresponding to a small relative total error of the calibration model and a Fitting Model Index of the calibration model that is close to 1. The system may be adapted so that computation of a tolerance interval is frequentist or Bayesian. The reference level can be the concentration or amount of the physical or chemical parameter determined by the reference analytical method.

The system may be adapted so that computation of the Fitting Model Index corresponds to the geometric mean of the dosing range, precision and trueness indexes and its value range from 0 to 1 depending on the fit quality.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. The mere fact that certain measures are recited in mutually different dependent claims does not indicate that a combination of these measures cannot be used to advantage. A single unit may fulfil the functions of several items recited in the claims. Any reference signs in the claims should not be construed as limiting the scope.

The invention claimed is:

1. A method of analyzing spectral data for the selection of the best calibration model from a plurality of calibration models, relating spectra of a substance to a physical or a chemical parameter of the substance, over a predetermined range of the physical or chemical parameters, comprising the steps of:

a) capturing spectral data of the substance with respective values of the physical or chemical parameter over the predetermined range;

b) building a plurality of calibration models, using the captured spectral data from step a, in dependence upon the values of the physical or chemical parameter, said plurality of calibration models being based on said spectral data and physical or chemical parameter from step a and using statistical resampling methods to assess a predictive quality of the models;

c) calculating tolerance intervals of the predicted results obtained using the models built in step b at reference level for each calibration model, d) displaying the tolerance intervals at each reference level for each calibration model; and e) selecting at least one of the calibration models upon a predefined criterion;

wherein the calibration model comprises a data regression model and a data pretreatment;

wherein the data regression model comprises any spectral data pretreatment followed by selecting at least one of the following available choices comprising a multiple linear regression model, a partial least squares model, a principal component regression model and an artificial neuronal network model;

wherein the predefined criterion comprises at least one of the following available choices comprising a tolerance interval corresponding to a small relative error of the calibration model, an acceptance limit of the physical parameter corresponding to a small relative total error of the calibration model and a Fitting Model Index of the calibration model that is close to 1; and wherein the methodology to compute a tolerance interval is selected from the available choices of frequentist or Bayesian.

2. The method according to claim 1, wherein the spectral data comprise near infrared spectra data.

3. The method according to claim 1, wherein the data pretreatment comprises any one of a standard normal variate treatment, a Savitzky-Golay smoothing filter with no derivative and/or a first derivative and/or a second derivative operation, a multiplicative scatter correction, an orthogonal signal correction or raw data.

4. The method according to claim 1, wherein the tolerance interval corresponds to either a beta expectation tolerance interval or a beta-gamma content tolerance interval.

5. The method according to claim 1, wherein step d) comprises at least one of printing on a printer, plotting on a plotter, displaying on a video display unit and projecting onto a screen.

6. The method according to claim 1, wherein the reference level is the concentration or amount of the physical or chemical parameter determined by the reference analytical method.

7. The method according to claim 1, wherein the methodology to compute the Fitting Model Index corresponds to the geometric mean of the dosing range, precision and trueness indexes and its value range from 0 to 1 depending on the fit quality.

8. A non-transitory computer readable medium product comprising code segments that when implemented on a computing system implement the methods of claim 1.

9. The computer readable medium product of claim 8 stored on machine readable signal storage means.

10. A computer based system for analyzing spectral data for the selection of a calibration model, relating spectra of a substance to a physical or a chemical parameter of the substance, over a predetermined range of the physical or chemical parameter, comprising:
   a) means for capturing spectral data of the substance with respective values of the physical or chemical parameter over the predetermined range,
   b) means for creating a plurality of calibration models using the captured spectral data in dependence upon the values of the physical or chemical parameter based on the calibration data using statistical resampling methods,
   c) means for calculating tolerance intervals of the results at each reference level for each calibration model,
   d) means for displaying the tolerance intervals at each reference level over the predetermined range for each calibration model, and
   e) means for selecting at least one of the calibration models upon a predefined criterion;
   wherein the calibration model comprises a data regression model and a data pretreatment;
   wherein the data regression model comprises any spectral data pretreatment followed by selecting at least one of the following available choices comprising a multiple linear regression model, a partial least squares model, a principal component regression model and an artificial neuronal network model;
   wherein the predefined criterion comprises at least one of the following available choices comprising a tolerance interval corresponding to a small relative error of the calibration model, an acceptance limit of the physical parameter corresponding to a small relative total error of the calibration model and a Fitting Model Index of the calibration model that is close to 1; and
   wherein the methodology to compute a tolerance interval is selected from the available choices of frequentist or Bayesian.

* * * * *

UNITED STATES PATENT AND TRADEMARK OFFICE
CERTIFICATE OF CORRECTION

PATENT NO.        : 8,494,818 B2
APPLICATION NO.   : 12/736929
DATED             : July 23, 2013
INVENTOR(S)       : Hubert et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 115 days.

Signed and Sealed this

Fifteenth Day of September, 2015

Michelle K. Lee
*Director of the United States Patent and Trademark Office*